United States Patent [19]

Dellacoletta et al.

[11] Patent Number: 5,719,295

[45] Date of Patent: Feb. 17, 1998

[54] PROCESS FOR PREPARING BIS(ETHER ANHYDRIDES) USING ALKYLAMINE DERIVED BISIMIDES HAVING LOW MELTING TEMPERATURES

[75] Inventors: Brent Dellacoletta, Evansville; Roy Ray Odle; Thomas L. Guggenheim, both of Mt. Vernon; Ronald A. Greenberg, Evansville, all of Ind.; James P. Barren, Scotia, N.Y.; Joseph A. King, Schenectady, N.Y.; Sunita Singh Baghel, Rensselaer, N.Y.; Deborah A. Haitko, Schenectady, N.Y.; David G. Hawron, Clifton Park, N.Y.

[73] Assignee: General Electric Company, Pittsfield, Mass.

[21] Appl. No.: 652,067

[22] Filed: May 23, 1996

Related U.S. Application Data

[62] Division of Ser. No. 250,736, May 27, 1994, Pat. No. 5,536,846.

[51] Int. Cl.⁶ .................................. C07D 209/12
[52] U.S. Cl. .................. 548/480; 548/461; 548/473; 548/481; 549/252
[58] Field of Search ........................... 548/480, 481, 548/473, 461; 549/252

[56] References Cited

U.S. PATENT DOCUMENTS

| | | | |
|---|---|---|---|
| 3,879,428 | 4/1975 | Heath et al. | 260/346.3 |
| 3,957,862 | 5/1976 | Heath et al. | 260/520 E |
| 4,020,089 | 4/1977 | Markezich | 260/326 R |
| 4,202,993 | 5/1980 | Takekoshi | 568/723 |
| 4,257,953 | 3/1981 | Williams, III et al. | 260/326 R |
| 4,302,616 | 11/1981 | Williams, III et al. | 568/722 |
| 4,318,857 | 3/1982 | Webb et al. | 260/346.3 |
| 4,599,429 | 7/1986 | Odle | 548/481 |
| 4,902,809 | 1/1990 | Groeneweg et al. | 548/481 |
| 4,921,970 | 5/1990 | Odle | 548/480 |
| 5,132,423 | 7/1992 | Brunelle et al. | 548/473 |
| 5,155,234 | 10/1992 | Odle | 549/243 |
| 5,206,429 | 4/1993 | Odle | 548/473 |

OTHER PUBLICATIONS

CA 84: 121421 f Nitro Derivatives of Aromatic Compounds., Cook et al., p. 505, 1976.

CA 84: 121646 h N–methyl Nitro Phthalimides., Cook et al. p. 524, 1976.

CA 119: 203290 t Preparation of 4–nitro–N–methylphthalimide., Dorogov et al., p. 881, 1993.

*Primary Examiner*—Joseph McKane

[57] ABSTRACT

A process for making bis(ether anhydrides) employs alkylamines having low melting temperatures thus allowing for novel intermediate process steps for preparing bis(ether anhydrides). The alkylamines have alkyl groups which contain at least three carbon atoms and have boiling temperatures in the range of 48° to 250° C. at atmospheric pressure. As a result of using these amines, liquid alkylamines now can be employed in the imidization process step. The N-alkyl nitrophthalimides prepared from the recovered imidization product according to this invention can now be purified using liquid/liquid extraction or vacuum distillation. The alkyl nitrophthalimides prepared according to this invention provide for displacement reactions which now can be run at a high solids level. Likewise, the exchange reaction can be run at a higher solids level, and thus achieves an efficiency level which is higher than conventional processes.

17 Claims, No Drawings

PROCESS FOR PREPARING BIS(ETHER ANHYDRIDES) USING ALKYLAMINE DERIVED BISIMIDES HAVING LOW MELTING TEMPERATURES

This is a divisional of application Ser. No. 08/250,736 filed on May, 27, 1994, now U.S. Pat. No. 5,536,846.

BACKGROUND OF THE INVENTION

1. Field of the Invention

This invention relates generally to processes for preparing bis(ether anhydrides). In particular, safer and more efficient imidization, nitration, displacement and exchange reactions leading to the preparation of bis(ether anhydrides) are made possible as a result of conducting the imidization step with a liquid alkylamine wherein the alkyl group of the alkylamine preferably contains at least three carbon atoms.

2. Brief Description of the Background Art

Processes for preparing bis(ether anhydrides) are well known. Bis(ether anhydrides) are intermediates used to prepare polyetherimides which are well known components for plastic automobile parts and the like. Biphenol dianhydride and bisphenol A dianhydride are two frequently used intermediates. Processes for preparing such bis(ether anhydrides) can involve four intermediate steps. Those process steps comprise:

(1) an imidization step in which "make-up" n-alkyl phthalimide is synthesized from an alkylamine and phthalic anhydride, (2) a nitration step in which the n-alkyl phthalimide is nitrated, (3) a displacement reaction step in which the nitro substituent on the phthalimide ring is displaced and a bisimide is formed, and (4) a transformation step ("exchange reaction") in which the bisimide is transformed to dianhydride, preferably by reacting the bisimide with phthalic anhydride in the presence of triethylamine and water. The exchange also can be carried out by a process in which the bisimide is hydrolyzed, acidified and dehydrated to form the desired bis(ether anhydride). The resulting product can then be employed to prepare polyetherimides such as ULTEM® polyetherimides commercially available from General Electric Co. See, for example, U.S. Pat. No. 4,020,089 to Markezich (imidization); U.S. Pat. Nos. 4,902,809 to Groenaweg et al. and 4,599,429 to Odle (nitration); U.S. Pat. No. 4,257,953 to Williams, III et al. (displacement); and U.S. Pat. Nos. 3,957,862 and 3,879,428, both to Heath et al. (exchange reaction).

As with many commercial chemical synthesis processes, there remains a need and desire to improve the process from economic, environmental and overall efficiency aspects. We have specifically identified the use of methylamine in the preparation of the "make-up" phthalimide as an aspect of the existing process that, if avoided, could lead to process improvements.

The disadvantage presented by methylamine is twofold. Methylamine is not only toxic, but also its boiling temperature is relatively low, therefore rendering it gaseous at temperatures under which make-up phthalimide is synthesized. As a result, methylamine requires special toxic gas equipment when preparing the "make-up" phthalimide. In addition, at least two condensers are typically employed to condense methyl phthalimide to its more practical liquid form. The liquid condensate which forms in the condenser, however, solidifies on the walls of the condenser and creates blockages. As a result, the condenser is taken off stream and another condenser is utilized while the blocked condenser is heated to remove the residue. The second condenser is similarly removed once it becomes blocked. A safer and more efficient process thus is desired.

In addition, the resulting methyl-derived phthalimide has a high melting temperature and thus must be stored at temperatures of about 133° C. or higher in order to keep the "make-up" phthalimide in liquid phase for further processing.

The overall efficiency of nitrating methyl phthalimide is relatively low because recycling the methyl phthalimide nitrating agent requires a relatively inefficient nitration concentration system. After nitrating the phthalimide ring to form a methylnitrophthalimide, the nitrophthalimide product and the nitrating agent are recovered. N-methyl nitrophthalimide usually is recovered by removing the nitrating agent and solvent via a falling film evaporator. A falling film evaporator, however, is only capable of concentrating N-methyl nitrophthalimide to about 50% solids. Attempts to remove any more nitric acid results in the precipitation of the methylnitrophthalimide product from the solution. As a result, methylnitrophthalimide reaction product solution is quenched into weak nitric acid. The resulting precipitate is washed in countercurrent fashion on a belt filter. In order to be recycled for later nitration, the remaining dilute nitric acid must be recovered in a nitric acid concentrator and sulphuric acid concentrator (NAC/SAC) system. Both the belt filter and NAC/SAC system are quite inefficient as they employ about two pounds of water for every one pound of methylnitrophthalimide produced.

The N-methyl nitrophthalimide product then is dried by partitioning the product from water into toluene. Handling environmentally hazardous organic solvents thus is required. Organic solvents also are required in the displacement reaction which forms the bisimide.

Further problems and inefficiencies are presented when extracting the by-products created by the displacement reaction of methylnitrophthalimides with the salts of sodium bisphenol. These by-products typically are extracted at temperatures of about 85° C. using alkali solutions at concentrations of about 1 to about 5% alkali. Extractions with such solutions can cause hydrolysis of the desired bisimide product, and as a result, the time, temperature and alkali concentration must be monitored in order to minimize such hydrolysis.

Displacement reactions with N-methyl nitrophthalimides also can be carried out to only about a 22% solids level in the bisimide reaction mixture. If the reaction is allowed to run to a higher solids level, bisimide product precipitates out of the solvent. In addition, substantial amounts of organic solvents are required for processing mixtures at these levels of solids. Running this reaction to a higher, and thus more efficient, solids level thus is difficult and limited.

Inefficiencies also occur in the exchange reaction with bisimides derived from methyl amines. The reaction influent of the preferred exchange reaction comprises bisimide and excess phthalic anhydride and triethylamine, as well as the accompanying transimidization products of both reactants, e.g., bisimide, imide acid, diacid, phthalic acid, and N-methyl phthalimide. By-products typically are removed by extracting the imide products into toluene, thereby driving the equilibrium and leaving only tetra acid salts in the aqueous phase. These acid salts then are stripped of water and triethylamine to leave the desired dianhydride. Methyl-derived bisimides, however, have a limited solubility in toluene, and, therefore, throughput of reaction product solids in the exchange reaction of these bisimides is low, e.g., about 12%. Greater efficiency is desired.

SUMMARY OF THE INVENTION

The foregoing disadvantages are overcome by the present invention. The inventive method includes the steps of (a) synthesizing an N-alkyl phthalimide from (i) liquid alkylamine and (ii) liquid anhydride; (b) nitrating the N-alkyl phthalimide to produce a N-alkyl nitrophthalimide; (c) purifying the N-alkyl nitrophthalimide employing liquid/liquid extraction or vacuum distillation; (d) drying the extracted or distilled N-alkyl nitrophthalimide under substantially solventless conditions; (e) reacting the dried N-alkyl nitrophthalimide with a bisphenol alkali salt to form a bisimide wherein the solids level of the reaction is at least 30% by weight; (f) hydrolyzing the bisimide to form a tetra-acid salt; and (g) acidifying and dehydrating the tetra-acid salt to form the bis(ether anhydride).

The liquid alkylamine employed in the imidization step preferably contains three or more carbon atoms. As explained more fully below, the presence of such an alkyl group in the various reaction intermediates further improves the total efficiency of the bis(ether anhydride) preparation.

Butyl and propyl amines are preferred liquid alkylamines in some instances because of their relatively low cost. When employing a continuous process of preparing bisimides and/or bis(ether anhydrides) substantial cost savings thus can be realized. Butyl, propyl and hexyl amines are preferred when preparing biphenol dianhydrides.

One or more of the following novel process steps according to this invention also can be employed as an intermediate step in conventional processes for preparing a bis(ether anhydride).

For example, the "make-up" phthalimide now can be prepared from liquid alkylamines, as opposed to gaseous amines, thereby alleviating the need for the gas-handling equipment used for methylamine.

N-alkyl nitrophthalimide suitable for preparing a bis(ether anhydride) for example, can now be prepared by (a) providing a N-alkyl phthalimide and a nitrating agent; (b) removing substantially all of the nitrating agent; and (c) purifying the N-alkyl nitrophthalimide employing liquid/liquid extraction or vacuum distillation. This process thus alleviates the need to run an inefficient belt filter process. As mentioned earlier, the belt filter process consumes substantial amounts of water. Moreover, the extracted or distilled N-alkyl nitrophthalimide now can be dried under substantially solventless conditions, which also reduces the amount of water consumption during the nitration process.

Alkylnitrophthalimides according to this invention (wherein the alkyl group has three or more carbon atoms) have a relatively high solubility and provide for bisimide preparation reaction mixtures having a solids level previously not obtained with methyl nitrophthalimides. Substantial amounts of solvent thus are avoided and higher throughput of substantially pure bisimide product is provided when employing this invention. As a result, bisimides suitable for preparing a bis(ether anhydride) now can be prepared by (a) providing a N-alkyl nitrophthalimide and a bisphenol alkali metal salt; (b) reacting the N-alkyl nitrophthalimide and the salt at a solids level of at least about 30% by weight solids to form a substantially pure bisimide; and (c) extracting the bisimide. The bisimide also can be prepared under substantially solventless conditions, e.g., at a 100% solids level.

As mentioned above, any or all of these steps can be employed in a bis(ether anhydride) preparation process. In the alternative, one of the steps described above can be employed in a bis(ether anhydride) preparation process which otherwise comprises conventional steps.

DETAILED DESCRIPTION

The melting temperatures of the alkylamines employed according to this invention allow the phthalimide synthesis step of this invention to employ liquid reactant. The alkylamines according to this invention are liquids at ambient conditions and have boiling points in the range of 48° C. to 250° C. The alkyl groups of these alkylamines contain three or more, and preferably three to six carbons.

N-alkyl phthalimide synthesis typically is conducted at a temperature in the range of 155° to about 170° C. Water created during the N-alkyl phthalimide synthesis is removed employing conventional techniques, e.g., simple distillation at 155° C.

While methyl-substituted phthalimide is isolated and stored at approximately 180° C. under nitrogen, the N-alkyl phthalimides prepared according to this invention can be stored as a melt, for example, at about 40° C., i.e., the approximate melting point of N-butyl phthalimide. The alkylphthalimide according to this invention has a formula

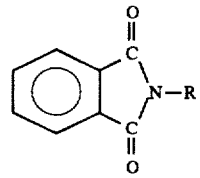

wherein R is at least a $C_3$, and preferably a $C_3$–$C_6$ alkyl.

The choice of the number of carbon atoms in the alkyl group "R" depends on the desired reaction product, process speed and efficiencies for the particular process being conducted. Lower alkylamines such as n-propylamine and n-butylamine are particularly preferred. The propyl group provides for materials which are easier to purify. The propyl-derived products produced during nitration reactions in the preparation of bisphenol A dianhydride, for example, are easier to purify than butyl-derived products. As discussed in more detail below, purification of butyl-derived nitration products involves additional steps in order to achieve a commercially acceptable impurities level. N-hexylamine is sometimes preferred when preparing biphenol bisimide.

The butyl-derived materials are more soluble in the solvents typically used in the various reactions. The higher solubility allows for reactions at higher solids levels and accordingly makes the process according to this invention more efficient. The improved solubility of the butyl-derived materials over propyl-derived materials is especially highlighted in the preparation of biphenol bisimides. For this reason, the butyl-derived materials are preferred when preparing such dianhydrides. The solubility of various alkyl-derived imides, nitroimide, bisimides, etc., in toluene are disclosed in Table 5. The boiling temperatures and melting temperatures of the compounds according to this invention also are included in that table.

Other suitable alkyl groups include n-hexyl and t-butyl. As mentioned above, the selection of a particular alkylamine depends on several factors familiar to those of ordinary skill in this field who will be able to make such selection based on the teachings herein.

An N-alkyl phthalimide prepared according to this invention is nitrated to prepare N-alkyl nitrophthalimides. The N-alkylphthalimide is nitrated using known processes or by using the nitration process according to this invention. Known methods of nitration are described in U.S. Pat. Nos. 4,902,809 and 4,599,429. The nitration process according to this invention is described below.

Suitable nitrating agents for nitrating the N-alkylphthalimide invention include a nitric acid solution having a concentration of at least about 94% and preferably a concentration in the range of from about 97.5 to about 100% by weight, with the balance being water. While nitric acids of lower concentration are useful for the nitration process, the use of such concentrations results in processes which are too slow to be cost effective. Nitric acid solutions of at least 94% are available commercially. In the alternative, such solutions may be prepared by known concentrating methods from more widely available commercial nitric acid of 60 to 67% concentration. The concentrated nitric acid also may be mixed with another concentrated acid such as sulfonic acid to prepare a nitrating agent suitable for this invention.

The amount of concentrated nitric acid used in the nitrating agent should be at least a stoichiometric amount necessary to attach one $NO_2$ group on the aromatic nucleus of the N-alkylphthalimide. Generally, the weight ratio of nitric acid to the N-alkylphthalimide should be from about 0.4 to about 50, preferably from about 5 to about 30, most preferably from about 9 to about 15. Lower or higher amounts of nitric acid also may be used in the process of the present invention. Lower amounts of nitric acid, however, result in poor yields and too slow a reaction rate to be cost effective. Higher amounts of nitric acid may result in unnecessary decomposition of concentrated nitric acid and increased cost for such acid and its recycling.

The N-alkylphthalimide may be added to the reactor in any suitable form, e.g., powder, flake, etc., but preferably in liquid form.

The concentrated nitric acid and the N-alkylphthalimide are mixed together in a reactor or reactors preferably equipped with a stirrer and means for heating or cooling the reactor. The reactor(s) may be such as to allow for either batch or continuous processing.

Specific variations in the design of the process systems employed to practice the nitration according to the present invention are known to those skilled in the art. For example, it is possible to use one or more reactors in series or parallel which operate in the plug flow mode with or without radial mixing and with or without heating or cooling. Alternatively, it is possible to use one or more reactors in series or parallel which operate in the back mixing mode, again with or without heating and cooling and operating in a batch or continuous mode. Finally, it also is possible to use a combination of reactors with features of both the foregoing. The nitration reaction mixture's energy content, especially at lower nitric acid ratios, also must be taken into account when designing the process equipment.

The mode of mixing and the sequence of addition of reactants is not critical to the present invention. Feed of the reactants may either be into the first reactor or be portioned among the reactors if more than one reactor is used, or they may be entered at different locations of the reactor or reactors. Further, the reactants may be pre-mixed before entering the reaction process or they may be fed separately. It also is possible that one or both reactants are brought to the desired reaction temperature prior to mixing or entering the reactor.

Generally, the reaction temperature should fall within the range of from about −20° C. to the boiling point of nitric acid, preferably from about 10° C. to about 70° C., most preferably from about 20° C. to about 60° C. More specifically, the actual temperature to be employed is dependent upon the desired rate of reaction and the desired end products, e.g., the desired ratio of the 4-isomer, i.e., 4-nitroalkyl phthalimide, to 3-isomer, i.e., 3-nitroalkyl phthalimide, formed in the products.

Temperatures outside the range of temperatures disclosed above also may be employed with the present process. However, lower temperatures result in a reaction rate which is too slow to be cost effective, whereas higher temperatures require operation at above atmospheric pressure to prevent boiling and subsequent loss of nitric acid.

While the temperature at which the reaction is run has a significant impact on reaction rate, the specific reactants used and the ratio of reactants in the reaction mix also influence the reaction rate. With respect to the latter, the higher the concentration of the nitric acid in the initial mix or as added during continuous processing the faster the reaction rate. The specific alkyl group on the N-alkylphthalimide also is found to influence reaction rate. Finally, with respect to the ratio of the reactant mix, it is found that the rate of reaction increases as the ratio of nitric acid to N-alkylphthalimide increases. The most dramatic reaction rate increase, in this respect, being noted as the reactant ratio approaches about 10.

Thus by varying any one or all of the foregoing, one may significantly increase or decrease the time for which the reaction should run to obtain optimum yield. In general, with a reaction run at a temperature within the preferred range, e.g., 20° C.–60° C., up to about 90% or greater yield may be obtained within three hours. Optionally, these yields may be increased further by allowing the reaction mix to stand for a period of time prior to separation.

The pressure range under which the nitration process operates may vary from vacuum to above atmospheric pressure. Process and safety concerns may dictate operating the process under slight vacuum. Such conditions, however, depend on the type of reactor or reactors employed. Otherwise, the process is generally run at about atmospheric pressure.

The desired reaction products of this invention comprise primarily the 3- and 4-isomers of the respective N-alkyl nitrophthalimide. The specific ratio of the 3- and 4-isomers is largely dependent upon the temperature at which the reaction is run. For example, the ratio of 4- to 3-isomer may vary from about 16:1 at about 60° C. to about 26:1 at about 15° C. The weight ratio of starting reactants also may have a slight influence on the isomer ratio.

The ratio of 4- to 3-isomer may also affect the melting temperature of the N-alkyl nitrophthalimide. Compositions comprising primarily 3-isomers have lower melting points than those compositions comprising primarily 4-isomers. The lower melting temperatures of the former compositions, thus, make it easier to run the displacement reaction under solventless conditions as discussed later below.

N-alkyl nitrophthalimide resulting from the nitration reaction has a formula of

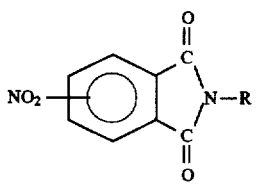

wherein R is an alkyl group preferably having at least three carbons, and preferably having three to six carbons.

The resulting N-alkyl nitrophthalimide is recovered by first removing, for later recycle, as much nitrating agent, e.g., strong nitric acid, as possible. When N-alkyl nitrophthalimide is prepared from a methyl amine, recovery is carried out until the reaction mixture contains about 50% solids, typically achieved by using a falling film evaporator. Subsequently, conventional processes quench the product-containing solution into weak nitric acid and the resulting precipitate then is washed in counter current fashion on a belt filter. The dilute nitric acid in such a system is recovered and recycled using a nitric acid concentrator and sulphuric acid concentrator (NAC/SAC) system. Typically, two pounds of water is used for every one pound of product.

When the N-alkyl nitrophthalimide is prepared from an alkylamine according to the process of this invention, e.g., a butyl amine, the N-alkyl nitrophthalimide can be concentrated in an evaporator wherein essentially all of the strong acid can be removed.

The higher nitric acid solubility of alkylnitrophthalimides according to this invention allows the alkylnitrophthalimide to remain in solution at higher solids levels during a falling film evaporator process. Water and nitrating agent thus can be removed to levels at which a more efficient liquid/liquid extraction or vacuum distillation can purify the nitrophthalimide product.

As indicated earlier, the alkyl nitrophthalimide product that is prepared according to this invention is stable at temperatures at which they are liquid, and thus can be recovered and purified in liquid/liquid extraction processes, e.g., conventional extraction processes using hot aqueous solutions or hot alkali solutions such as bicarbonate solution wherein a solution of the product is washed. The product also can be distilled at high vacuum and condensed to give purified molten product. It is not possible to effectively employ either of these two purification steps when synthesizing methyl-derived nitrophthalimides. Both processes are conducted at temperatures at which n-methyl-derived products melt and decompose.

Purification of butylnitrophthalimides by liquid/liquid extraction preferably comprises pretreating the butyl-derived material prior to extraction with concentrated acid, e.g., a small amount of concentrated sulfuric acid (acid that is about 95% by weight sulfuric acid), and then washing the treated material using dilute basic solution, e.g., about 0.2–1% by weight sodium bicarbonate. The sulfric acid pretreatment greatly enhances the purity of the product over that obtained from directly extracting such material. Without being held to any particular theory, the pretreatment and wash removes a butyl nitrate ester impurity resulting from the nitration reaction. Removing that impurity improves the yield of bisimide in the displacement reaction.

The N-alkyl nitrophthalimide then is dried. Conventional N-methyl nitrophthalimides are dried by partitioning the N-methyl nitrophthalimide from a water slurry into toluene. The toluene solution then is concentrated to about 30% solids, i.e., the solubility limit of N-methyl nitrophthalimide in toluene at 100° C. Residual water also is removed by azeotropic drying during this concentration step, as water is very detrimental to the displacement reaction which follows the nitration reaction.

When N-alkyl nitrophthalimides are prepared according to this invention, other drying steps can be used. Butyl-substituted nitrophthalimide is molten at a temperature of about 95° C. and can be dried in a column using heat and/or vacuum to remove residual water. On the other hand, if the solvent based drying system similar to that employed for the methyl-derived nitrophthalimides is to be employed, the nitrophthalimide can be dried under near solventless conditions, i.e., up to about 100% solids. As mentioned earlier, these solventless conditions are possible due to the melting and enhanced solubility characteristics of the products containing alkyl groups having at least 3 carbon atoms. The melting temperatures of the alkyl nitrophthalimides produced according to this invention are provided in Table 5. N-alkyl nitrophthalimides prepared from preferred alkylamines, e.g., amines derived from alkyls having 3 to 6 carbon atoms, have a melting temperature in the range of about 90° to about 135° C. and solubilities of at least about 11% by weight, and in a number of instances 50% or greater in toluene at room temperature. Once dry, the N-alkyl nitrophthalimide is further processed to prepare bisimide.

Bisimides are prepared through displacement reactions between the N-alkyl nitrophthalimide and salts of bisphenol compositions. Suitable bisphenol salts are those alkali metal phenoxide salts of the formula.

For instance, bisimides such as aromatic ether bisimides of the formula

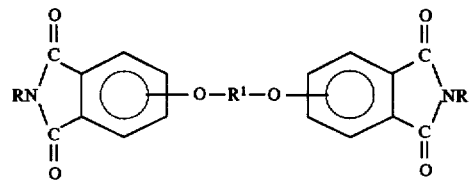

are prepared by heating the alkali metal bisphenol salt above and an N-alkyl nitrophthalimide of the formula,

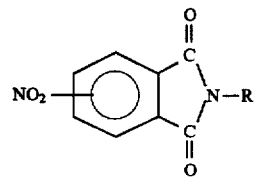

wherein $R^1$ is a $C_{(6-30)}$ aromatic organic radical, M is an alkali metal ion, R is an alkyl having at least 3 carbons, and preferably 3 to 6 carbons. The reaction of the salt and substituted phthalimide can be carried out in the presence of a nonpolar organic solvent and an effective amount of a phase transfer catalyst.

$R^1$ more particularly includes

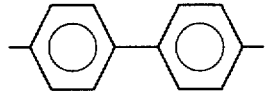

-continued

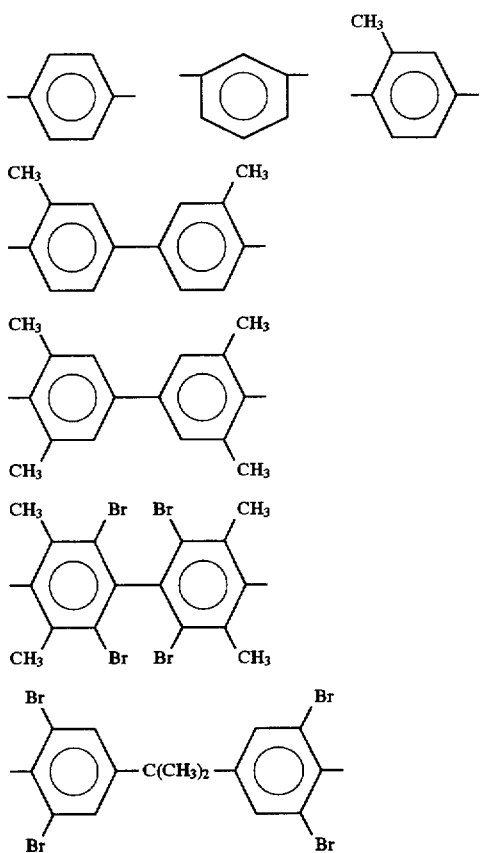

and divalent organic radicals of the general formula

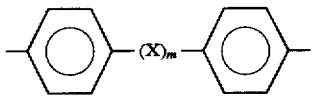

where X is a member selected from the class consisting of divalent radicals of the formula

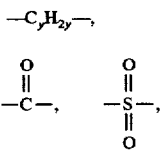

—O— and —S— —O—, and —S—, where m is 0 or 1, and y is a whole number from 1 to 5.

Some of the alkali salts of the above-described alkali phenoxide are sodium and potassium salts of dihydric phenols, for example, 2,2-bis-(2-hydroxyphenyl)propane,
2,4'-dihydroxyphenylmethane,
bis(2-hydroxyphenyl)methane,
2,2-bis-(4-hydroxyphenyl)propane hereinafter identified as "bisphenol-A" or "BPA",
1,1-bis-(4-hydroxyphenyl)ethane,
1,1-bis-(4-hydroxyphenyl)propane,
2,2-bis-(4-hydroxyphenyl)pentane,
3,3-bis-(4-hydroxyphenyl) pentane,
4,4'-dihydroxybiphenyl,
4,4'-dihydroxy-3,3,5,5'-tetramethylbiphenyl,
2,4'-dihydroxybenzophenone,
4,4'-dihydroxydiphenylsulfone,
2,4'-dihydroxydiphenylsulfone,
4,4'-dihydroxydiphenylsulfoxide,
4,4'-dihydroxydiphenylsulfide,
hydroquinone,
resorcinol,
3,4'-dihydroxydiphenylmethane,
4,4'-dihydroxybenzophenone,
and 4,4'-dihydroxydiphenylether.

Preferred nitrophthalimides are, for example, 4-nitro, N-butylphthalimide; 3-nitro, N-butylphthalimide; 4-nitro, N-hexylphthalimide; 3-nitro, N-hexylphthalimide; 4-nitro, N-propylphthalimide; and 3-nitro, N-propylphthalimide.

One method of preparing bisimide is to bring to reflux a heterogeneous mixture of an aqueous solution of alkali metal bisphenoxide salt and a nonpolar organic solvent having a boiling point of from 80° C. to 200° C. at 760 torr, with the removal of solvent until it can be recovered substantially free of water. An effective amount of phase transfer catalyst also is employed. Nonpolar organic solvents, such as toluene, can dissolve up to about 0.05% by weight water without affecting its clarity. Small amounts of residual water can therefore be readily detected. In forming the heterogeneous mixture, the order of addition of the nonpolar organic solvent and the aqueous solution of the alkali metal phenoxide salt is not critical. There is preferably used substantially stoichiometric equivalents of alkali metal hydroxide and bisphenol in forming the alkali metal phenoxide salt; however, up to a 0.5 mole % stoichiometric excess of alkali metal hydroxide can be tolerated without substantially adverse results in the displacement reaction. Other methods for preparing the alkali metal hydroxide salt are described in U.S. Pat. No. 4,202,993.

The phase transfer catalysts suitable for the displacement reaction are, for example, tetrabutylammonium bromide, tetrapropylammonium bromide, tetrabutylammonium chloride, tetrabutylammonium fluoride, tetrabutylammonium acetate, tetrahexylammonium chloride, tetraheptylammonium chloride, Aliquat 336 phase transfer catalyst (methyltrioctylammonium chloride, manufactured by the General Mills Company), tetrabutylphosphonium bromide, tetraphenylphosphonium chloride, hexabutylguanidium bromide, hexabutylguanidium chloride, hexaethylguanidium bromide, and hexaethylguanidium chloride.

The phase transfer catalyst can be utilized at from 0.0005 equivalent to 2 equivalents of the catalyst, per equivalent of alkali bisphenoxide and preferably from 0.01 to 0.05 equivalent. Nonpolar organic solvents which can be employed in the practice of the present invention include, for example, toluene, xylene, chlorobenzene and benzene.

Another method of preparing bisimide employs dipolar aprotic organic solvents, such as those described in U.S. Pat. No. 3,957,862 and U.S. Pat. No. 3,879,428, the contents of both incorporated herein by reference.

Reaction between the nitroimide and diphenoxide to produce the bisimide can be effected under an inert gas atmosphere such as nitrogen at 5° C. to 100° C. under substantially anhydrous conditions and in the presence of dipolar aprotic organic solvent such as dimethyl sulfoxide, N,N-dimethylformamide, N-methylpyrrolidine, N,N-dimethylacetamide, etc. Mixtures of such solvents with non-polar solvents such as toluene, chlorobenzene, etc. also can be employed. Reaction time can vary between 1 minute to 100 minutes or more depending upon temperature, degree of agitation, etc. A proportion of from 1.8 to 2.5 moles of nitroimide, per mole of diphenoxide can be used.

While higher or lower amounts of the reactant will not substantially interfere with the formation of the desired bisimide, about 2 mols of the nitrophthalimide per mol the bisphenoxide salt preferably is used in preparing the bisimide.

The bisimide can be recovered from the reaction mixture and purified by a variety of procedures. One procedure includes dissolution of the bisimide with an organic solvent such as toluene and then washing or extracting with alkali solution containing about 1 to about 5% by weight alkali, to remove by-products, e.g., monoimides, etc., and unreacted starting materials.

When N-alkyl nitrophthalimides are prepared according to this invention, the displacement reaction can be carried out at high solids levels, e.g., at 30% by weight, as well is levels in which the reaction is substantially solventless. The solubility of alkylnitrophthalimides having alkyl groups containing three or more carbon atoms allows such solids levels. That solubility also provides for the higher throughput of product in the displacement reaction. The solubilities of these compounds also allow for extractions of displacement reaction by-products at temperatures below the temperatures typically used with the methyl-derived products. Savings in energy costs thus can be realized as well. The solubilities of various alkylnitrophthalimides produced according to this invention are tabulated in Table 5 below. On the other hand, and as mentioned earlier, displacement reactions using N-methyl nitrophthalimide and, e.g., bisphenol-A disodium salt can effectively only be run to about 20% solids in the reaction mixture because of the methyl-derived product's limited solubility in toluene at 85° C.

Displacement reactions involving methyl-derived N-methyl nitrophthalimide and biphenoxide salts, when such reactions are run at solids levels of more than 20%, lead to products having unacceptable amounts of impurities, as well as incur increased costs due to processing the solid product which precipitates out of the reaction mixture at such solids levels. Reactions of biphenoxide salts with N-butyl-4-nitrophthalimide according to this invention, on the other hand, substantially avoid these problems and allow for a substantially pure displacement reaction product, e.g., product containing less than 1 part per million 4-nitro-N-alkylphthalimide, and much more flexibility in the displacement reaction.

When using solventless reactions according to this invention, the reaction product is washed at 95° C. with 0.8% alkali aqueous solutions, the alkali concentration of conventional wash solutions. The reaction products according to this invention also can be washed at lower temperatures, e.g., 85° C. or less, by using alkali solutions having higher alkali concentrations, e.g., 5% by weight alkali.

The carbon atom content of the alkyl group on the nitrophthalimide affects the displacement reaction as well. Propyl-derived nitrophthalimides, for example, are preferred in certain instances because such nitrophthalimides are easier to purify, thus providing a reactant that is more likely to produce a higher yield of bisimide. The corresponding nitrate ester discussed earlier with regard to the butyl-derived nitrophthalimide is not found. Butyl-derived nitrophthalimides, however, are preferred in some instances because of their lower melting points and higher solubilities in the solvents discussed above for the bisimide reaction.

The bisimide resulting from the displacement reaction can be further processed for introduction to an exchange reaction by removing solvent, if any, to give molten bisimide. Solvent is removed using conventional processes such as flashing off the solvent and holding the bisimide melt at approximately 260° C. This flashing step, however, need not be employed if a solventless displacement reaction is conducted using alkyls according to this invention. Moreover, the melt of bisimide prepared according to this invention can be held at lower temperatures, e.g., 100° C. for butyl-derived bisimides.

The exchange reaction can be conducted utilizing conventional techniques. Transformation of the bisimide preferably is carried out under known conditions by reacting the bisimide in its molten state with aqueous phthalic acid solution and triethylamine as described in U.S. Pat. No. 4,318,857 to Webb et al., the contents of which are incorporated herein by reference. It is preferable to run this reaction at a temperature in the range of about 180° C. to about 240° C. The resulting reaction product then is extracted with an organic solvent. The aqueous mixture then is stripped from the extraction solution to recover the bis(ether anhydride).

Other exchange techniques are described in U.S. Pat. Nos. 3,957,862 and 3,879,428, both incorporated herein by reference. For example, the bisimide is hydrolyzed with base to a tetra-acid salt, which is thereafter acidified to the tetra-acid. The tetra-acid then is dehydrated to the corresponding aromatic bis(ether anhydride).

Hydrolysis of the bisimide to the tetra-acid salt can be effected under reflux conditions in the presence of a base such as an alkali hydroxide, including sodium hydroxide. Reaction time can vary from 1 to 24 hours or more depending upon reactants, degree of agitation, temperature, pressure, etc. The organic amine by-product can be removed by standard procedures, such as steam distillation, decantation (when butyl-derived materials are used), etc. In addition, the rate of hydrolysis is greatly accelerated by carrying out the reaction at above atmospheric pressures at temperatures in the range of from 100° C. to 220° C.

The tetra-acid salt thereafter can be acidified with a mineral acid, such as a dilute aqueous solution of hydrochloric acid, etc. The resulting tetra-acid is dehydrated and recrystallized by standard techniques, e.g., refluxing with a dehydrating agent such as acetic anhydride.

In order that those skilled in the art will better able to practice this invention, the following examples are given by way of illustration, and not by way of limitation.

EXAMPLE 1

Synthesis of "Make-Up" N-Butylphthalimide

A 10-gallon stainless steel reactor equipped with a turbine blade impeller, cooling coil, distilling condenser, azeotropic separator, thermocouple probe and means to maintain a nitrogen atmosphere, was charged with 15.335 kg (103.53 moles) phthalic anhydride. N-butylamine (7.663 kg, 104.57 moles) from a pressure vessel was slowly added to the reactor which was at room temperature, e.g., about 25° C. The resulting exothermic reaction between the amine and phthalic anhydride was continued until the temperature in the reactor rose to 90° C., at which time addition of amine was complete. The reaction mixture was then heated, with removal of water, for a 5 hour period until the temperature of the mixture reached 200° C. The reaction mixture then was maintained at 200° C. for 2 hours. The resulting product was vacuum distilled at a temperature ranging from 150°–155° C. and at a pressure of 20 mm, to afford a liquid which solidified. The melting point of the solid was about 34° to 35° C. and was produced at a 95% yield.

EXAMPLE 2

Synthesis of Nitro-N-Butylphthalimide

A 3-necked, 5-liter round-bottomed flask, equipped with a mechanical stirrer, was charged with 4,259 g (67.6 moles)

of 99% nitric acid. To the flask was added 524.9 g (2.58 moles) N-butylphthalimide as a liquid at such a rate as to keep the reaction temperature under 40° C. The addition of the N-butylphthalimide was completed in about a half hour. The reaction was then heated for six hours to 50° C. in a temperature controlled water bath. The reaction product was then fed to a wiped film evaporator that was heated at 100° C. and under vacuum (30 mm). The bulk of the nitric acid was distilled off and the liquid product, i.e., 4-nitro-N-butylphthalimide and 3-nitro-N-butylphthalimide in a ratio of about 25:1, was isolated as a liquid which rapidly solidified to about 98% solids upon cooling in the collection vessel. Depending on the operation of the evaporator, the residual nitric acid in the product was less than 3% by weight, and was as low as 0.1% by weight.

EXAMPLE 2A

Alternative Synthesis of Nitro-N-Butylphthalimide

A 100-mL 3-necked, round-bottomed flask was charged with 67.6 g of 96% sulfuric acid and 20 g of N-butylphthalimide. An addition funnel was charged with 7.36 g of 96% sulfuric acid and 8.4 g of 96% nitric acid. The reaction was run at 19.3% solids by weight. The reaction vessel was heated to 35°–40° C. using an external water bath. When the N-butylphthalimide had dissolved in the sulfuric acid, the nitric/sulfuric acid mixture was added dropwise at a rate such that the temperature in the vessel did not exceed 50°–55° C. The addition time was typically 0.5 hours. The vessel was maintained at 45° C. for at least 3 hours at which time the reaction was determined by HPLC analysis to be completed.

The nitration mixture was then poured into water such that the strength of the sulfuric acid was 50% by weight. The mixture was heated to 100° C. and stirred for 5 minutes. The stirring was ceased and a two phase liquid liquid system resulted. The bottom aqueous phase was drawn off using a pipette. The organic phase solidified upon cooling to give a 90–94% yield of nitro-N-butylphthalimide. The ratio of 4-nitro-N-butylphthalimide to 3-nitro-N-butylphthalimide was 15–20:1. The product phase could then be purified using conventional procedures.

The above nitration reactants were also run at 30% solids, resulting in 3% starting material and _1% of oxidation side products present in the final product. The same nitration run at 20% solids resulted in a product containing <0.1% starting material and 4–5% oxidation side products (products where the butyl group had been oxidized yet contained a 4-nitro group on the aromatic ring). It is therefore desirable to run the mixed acid nitration at 30% solids to minimize the amount of yield loss through oxidation side chemistry. The unreacted N-butylphthalimide can ultimately be recovered in the exchange loop. A 30% solids level reaction can also be run by using less sulfuric acid.

The purified products can then be used in a phase transfer catalyzed reaction with BPA disodium salt to afford >98% butyl bisimide.

EXAMPLE 3

Liquid/Liquid Washing of Nitro-N-Butylphthalimide

About 500 g of product isolated from the wiped film evaporator in Example 2 was charged to a one liter jacketed resin kettle, equipped with a mechanical stirrer. The product was melted by hot oil which was recirculated through the jacket at 110° C. A nitrate ester impurity, i.e., the nitrate ester of 4-nitro-N-(3-hydroxybutyl)phthalimide, then was removed by converting the impurity to its corresponding alcohol and removing the alcohol with a basic aqueous wash. In particular, the nitrate ester impurity was converted to an alcohol by treating the material with a 95–98% by weight sulfuric acid at 100° C. for 1 min. The sulfuric acid solution was added to the melted product in an amount of about 1% by weight The product and converted alcohol were then washed by adding 500 mL of water at 100° C., agitating the components for 30 seconds, and then allowing the settling, e.g., for about 5–10 minutes, and separation of the neat product and aqueous phases.

The product was then washed with 500 mL of 0.2% aqueous sodium bicarbonate as described for the water wash above, with a final 500 mL water wash following the bicarbonate wash. Products from additional nitro N-alkyl phthalimide synthesis reactions were similarly washed with other dilute bases such as 0.1–2% aqueous disodium phosphate, 0.1–2% aqueous sodium carbonate and 0.1–2% aqueous sodium bisulfite.

The resulting washed product was then azeotropically dried with toluene and was then used, in a displacement reaction in which 10.0 g (0.0367 mole) sodium salt of bisphenol A was reacted with 18.23 g (0.0735 mole) of nitro-N-butyl phthalimide in 28 g toluene containing 0.22 g of $C_6B$ catalyst. The reaction gave 98% bisimide.

When the above displacement reaction was run without removing the nitrate ester impurity from the butyl-derived materials, very low yields of about 30–70% bisimide were obtained.

Yield loss, e.g., about 2–10% by weight, also was experienced when stronger, e.g., 2% by weight basic aqueous washes were used in the pretreatment step. The larger yield loss can be attributed to greater product hydrolysis that occurs with more base.

EXAMPLE 4

Alternative Washing of Nitro-N-Butylphthalimide

The product isolated in Example 2 was again treated with sulfuric-acid (1 wt % of 98% sulfric acid), but then dissolved in 0.1–1 volume equivalents of toluene with respect to the volume of product and washed with the aqueous sodium bicarbonate regents at 80° C. Yields of greater than 99% nitro-N-butylphthalimide were obtained.

EXAMPLE 5

Synthesis of Nitro-N-Propylphthalimide

N-propylphthalimide (50 g) was nitrated in 500 g 99% nitric acid to produce 4-nitro-N-propylphthalimide under conditions described in Example 2.

The reaction product was precipitated into water and then collected by filtration. The product then was liquid/liquid washed at 100° C. with three 50 ml portions of water and then azeotropically dried with toluene. The product (10 g) then was used in a displacement reaction as described in Example 3 to afford propylbisimide in 87% isolated yield.

EXAMPLE 6

Distillation of Nitro-N-Butylphthalimide

Materials washed according to Example 3 were distilled in a distillation column having one theoretical plate. The distillation was conducted at temperatures (and pressures) of 150° C. (0.1 mm), 170° C. (0.15 mm), and 185° C. (2 mm). The distilled material from each distillation was then used in a displacement reaction to give bisimide in yields ranging from about 97 to 99%.

The materials washed according to Example 3 also were distilled by using Kugelrohr distillation equipment. In the Kugelrohr distillation, 87.6 g of nitro-N-butylphthalimide was distilled at 190° C. at 1 mm to afford 84.1 g of material, i.e., about a 96% product yield as described in Example 3. In a subsequent displacement reaction, the product distilled by the Kugelrohr distillation resulted in about a 97% yield of bisimide.

EXAMPLE 7A

Synthesis of Butyl Bisimide

The following Examples 7A and 7B illustrate the preparation of Butyl Bisimide in dipolar aprotic solvent. For example, 22.8 g (0.1 mol) of bisphenol-A, 300 mL of dimethylsulfoxide, 100 mL of toluene, and 16.0 g of sodium hydroxide as a 50% aqueous solution (0.2 mol) is heated to reflux under a nitrogen atmosphere using a Dean Stark trap for 5 hours to remove the water from the system. The toluene is distilled from the vessel after the bulk of the water is removed until the temperature of the reaction mixture exceeds 145° C. In this way, dry bisphenol A disodium salt is prepared. The reaction is then cooled to 50°–100° C. To the dry salt solution is added 49.6 g (0.2 mol) of dry 4-nitro-N-butylphthalimide under nitrogen. The reaction is stirred for 30 minutes to 2 hours at 40°–130° C., at which time the reaction is complete as determined by HPLC analysis. The reaction mixture is then added to 1 liter of water at which time the butyl bisimide precipitates. The precipitate is collected via filtration and dissolved in 100–200 mL of toluene at 80° C. The organic phase is washed with 25–50 mL of 1% aqueous sodium hydroxide solution at 80° C. to effect purification of the product. The phase is separated and the solvent removed on a rotary evaporator under reduced pressure to afford a 92–97% yield of purified butyl bisimide (mp 91°–93° C.), suitable for the exchange reaction.

EXAMPLE 7B

Alternatively butylbisimide is prepared from the use of bisphenol A (BPA) disodium salt prepared in toluene. For example a 3-necked, 3-liter, round-bottomed flask is charged with 228.29 g (1 mol) of bisphenol A, 1 liter of water and 2 moles of sodium hydroxide. The mixture is heated at 90° C. under nitrogen to effect solution of the material as BPA disodium salt. The vessel is then charged with 1.5 liters of toluene, and the two phase system is brought to reflux with the use of a heating mantle. Water is removed from the reaction vessel with the use of a Dean Stark receiver. The bulk of the water is removed when no more water separated in the Dean Stark receiver. At this point, 750 mL of the toluene is distilled from the reaction vessel and then 1 liter of dry toluene is added back to the vessel. Again, toluene is distilled from the vessel (1 liter) to furnish a dry white slurry of precipitated BPA disodium salt in toluene. The percent solids of the resulting slurry is determined by taking a known weight of a representative sample of the material, removing the toluene via distillation, followed by heating under vacuum (150° C., 1 torr), and finally weighing the isolated amount of salt.

A portion of this salt slurry containing 10.0 g (36.8 mmol) is then charged to a 250 mL, 2-necked, round-bottomed flask equipped with a stir bar, a Dean Stark receiver topped with a reflux condenser and means for maintaining a nitrogen atmosphere. The flask is also charged with 150 mL of dimethylsulfoxide (or dimethylformamide). The reaction vessel is heated with an external oil bath, and the toluene is distilled from the pot. Once the bulk of the toluene is removed the temperature of the flask is lowered to 50°–70° C., then the flask is charged with 18.2 g (73.5 mmol) of 4-nitro-N-butylphthalimide. The reaction mixture is heated for 30 minutes to 3 hours at 40°–100° C., whereupon the reaction is judged complete using HPLC. The reaction mixture is then worked up as in Example 7A to afford a 90–96% yield of purified butyl bisimide, suitable for the exchange reaction.

EXAMPLE 7C

Synthesis of Butyl Bisimide a. Reaction Having a 25% Solids Level in Solvent

Bisimide was synthesized according to the displacement process disclosed in U.S. Pat. No. 4,257,953. In particular, two molar equivalents of dry nitro-N-butylphthalimide were reacted under reflux with 1 molar equivalent of a disodium salt of bisphenol A in toluene having 1 mol % phase transfer catalyst present. The reaction was conducted for 1.5 hours at 125° C. and a 25% solids level followed by dilute, i.e., 1% caustic washes.

b. Neat Reaction

One mole equivalent of dry bisphenol A disodium salt was reacted neat, i.e., solventless, with two equivalents of nitro-N-butylphthalimide in the presence of 1 mole % phase transfer catalyst. The reaction gave 94% yield of bisimide. The resulting product then was washed with dilute caustic media.

EXAMPLE 8

Comparison of Prior Art Bisimide Synthesis and Bisimide Synthesis According to This Invention a. Prior Art Synthesis of Bisimide from 4-Nitro-N-Methylphthalimide and Biphenol A 250 ml three-necked round bottom flask equipped with overhead mechanical paddle (teflon) stirrer, stopper and modified Dean-Stark Trap fitted with reflux condenser and nitrogen inlet was charged with 8.957 g (43.45 mmol) 4-nitro-N-methylphthalimide, 0.668 g (1.086 mmol, 2.5% catalyst) C6B catalyst, 0.500 g (3.242 mmol) biphenyl (as an HPLC internal standard) and 91.2 ml toluene before purging with nitrogen for 5 minutes. The Dean-Stark was modified to allow liquid to return from the bottom of the trap back into the reaction vessel. The trap was filled with calcium hydride sandwiched between a plug of cheesecloth below and glass wool above (to prevent calcium hydride from returning to the reaction vessel). The calcium hydride facilitated drying of the reaction solution.

The contents of the reaction vessel were heated in a 150° C. oil bath and toluene was refluxed through the hydride for 50–90 minutes before cooling to room temperature. The reaction vessel was stoppered and placed in a glove box under a nitrogen atmosphere.

Biphenol disodium salt (5.000 g, 21.72 mmol), which was preweighed into a sample vial, was then added to the reaction mixture. The vessel was capped, removed from the glove box, reattached to nitrogen and heated to reflux in a 150° C. oil bath. The point at which the solution reached reflux was defined at t=0 for kinetic purposes, and the reaction was monitored every 30 minutes via HPLC. The reaction was under reflux for 2.5 hours. Aliquots (approximately 0.50 ml) were removed through the reflux condenser using a 1.0 ml disposable glass pipet, diluted with 3 ml chloroform and 0.5 ml N,N'-dimethylacetamide and then filtered through a 0.45 micron frit prior to HPLC analysis. The reaction was allowed to cool to room temperature before being further processed. The product precipitated from the solution.

The solid from the toluene supernatant then was filtered, followed by rinsing with 50–100 ml toluene. The solid was air-dried on a Buchner funnel via suction for 40 minutes. The recovered solid weighed 14.69 g and contained about 3.0 g sodium nitrite. The solid was then slurried in 50 ml 0.8% NaOH for 10 minutes, filtered and then rinsed on the filter with 50 ml distilled and deionized water. The solids were then dried in a vacuum oven at a temperature of 110° C. and a pressure of 30 torr for 3 hours. The recovered solid weighed 10.64 g, representing a 97.1% yield of bisimide. The melting temperature of the solid was in the range of 205°–207° C.

b. Synthesis of Bisimide from 4-Nitro-N-Butylphthalimide and Biphenol

A 100 ml three-necked round bottom flask equipped with overhead mechanical paddle (teflon) stirrer, stopper and modified Dean-Stark Trap fitted with reflux condenser and nitrogen inlet was charged with 8.00 g (32.2 mmol) 4-nitro-N-butylphthalimide, 0.495 g (0.806 mmol, 2.5% catalyst) C6B catalyst, 0.400 g (2.59 mmol) biphenyl (as an HPLC internal standard) and 16.4 ml toluene before purging with nitrogen for 5 minutes. The Dean-Stark was modified to allow liquid to return from the bottom of the trap back into the reaction vessel. The trap was filled with calcium hydride sandwiched between a plug of cheesecloth below and glass wool above to prevent calcium hydride from returning to the reaction vessel. The calcium hydride facilitated drying of the reaction solution.

The contents of the reaction vessel were heated in a 150° C. oil bath and toluene was refluxed through the hydride for 50 minutes before cooling to room temperature. The reaction vessel was stoppered and placed in a glove box under a nitrogen atmosphere.

Biphenol disodium salt (3.71 g, 16.1 mmol), which was preweighed into a sample vial, was then added to the reaction mixture. The vessel was capped, removed from the glove box, reattached to nitrogen and heated to reflux in a 150° C. oil bath. The reaction was allowed to reflux for 2.5 hours before cooling to about 80° C.

The reaction product mixture was then washed using three 15.0 ml aliquots of an aqueous 0.8% (w/w) NaOH solution which had been preheated to 85° C. The washes were allowed to stir for 15 minutes before removing the aqueous layer via 10 ml pipet. The product biphenol bisbutylimide was recovered using a Buchi rotary evaporator. About 9.0 g of product was recovered with a corresponding yield of about 95%. The melting temperature of the product was in the range of 170°–172° C.

95–99% isolated yields were obtained from reactions using 1.0–2.5% hexabutylguanidinium bromide as the phase transfer catalyst. The reaction employing this catalyst was run according to conditions disclosed in U.S. Pat. No. 5,132,423, the contents of which are incorporated herein by reference.

c. Solubilities of Methyl-Derived Biphenol Bisimide v. Butyl-Derived Biphenol Bisimide The solubilities (and melting points) of butyl-derived bisimides and methyl-derived bisimides were measured. The solubilities of the alkyl-derived materials below, i.e., bisalkylimides of biphenol dianhydride in toluene at 80° C. This temperature represents the temperature at which the toluene phase of the displacement reaction is washed with dilute NaOH.

As indicated in Table 1 below, the solubility of the methyl-derived material was equal to or less than 1% by weight in toluene. Because commercially viable processes are run at higher percent solids, the methyl-derived products precipitate out of the reaction mixture in those processes, thereby requiring the methyl-derived products to be isolated by filtration, followed by slurry washes of the solid product. The handling of solid products on the scale of commercial processes therefore incur inefficiencies.

TABLE 1

Comparison of the Melting Points and Solubilites in Toluene at 80° C. of Various Bisalkylimides of Biphenol Dianhydride

| Parameter | Methyl | Ethyl | n-Propyl | n-Butyl | n-Hexyl | Cyclohex |
|---|---|---|---|---|---|---|
| Point (°C.) | 205–207 | 211 | 211 | 172–174 | 136 | 246–250 |
| Solubility in Toulene at 80° C.* | ≦1% | 7% | 5% | 20% 20% | >50% ~80% | b |

*Solubility is given in % solids = (weight of bisimide)/(weight of bisimide + weight of toluene).
bThe solubility was determined to be <5% solids in refluxing toluene.

d. Purity of Methyl-Derived Biphenol Bisimide v. Butyl-Derived Biphenol Bisimide Solid impurities present in the reaction mixture for preparing bisimides contaminated the solid bisimide product when the product precipitates out of solution during processing and reflux. Many of these impurities cannot be washed free of the product prior to the exchange reaction because the washing techniques are only effective for washing the surface of the particles. As a result, the outcome of the exchange reaction is adversely affected when the bisimide product is introduced to the exchange reaction mixture. The bisimide product derived from butyl materials do not incur these problems because the butyl-derived product is soluble enough to remain in solution during processing at reflux. The butyl-derived product therefore is in solution thereby avoiding the costs of processing substantial amounts of solid products. The commingling of product with impurities also is minimized.

The analysis provided in Table 2 below is exemplary of the purity of methyl-derived bisimides of the prior art and butyl-derived bisimides produced according to this invention. The methods used to conduct the analysis also are indicated below.

TABLE 2

Comparison of Purities of Product Biphenol Bisimides from Butyl vs. Methyl Processes

| Component | Butyl Bisimide[a] | Methyl Bisimide[b] |
|---|---|---|
| Biphenol[c] | 0 | 100–1000 ppm |
| 4-Nitro-Np butylphthalimide[c] | — | — |
| 4-Nitry-N-methylphthalimide[c] | — | 500 ppm |

TABLE 2-continued

Comparison of Purities of Product Biphenol Bisimides from Butyl vs. Methyl Processes

| Component | Butyl Bisimide[a] | Methyl Bisimide[b] |
|---|---|---|
| Monoimide[c] | 0 | 30–200 ppm |
| Nitride[c] | <1 ppm | 200–400 ppm |
| Na[d] | 12.6 ppm | >500 ppm |
| Fe[d] | 2.1 ppm | e |
| Zn[d] | 3.2 ppm | e |

[a]Butylimide prepared according to Example 8(b) herein.
[b]Methylimide prepared according to Example 8(a) herein.
[c]Measured by high pressure liquid chromatography (HPLC) vs biphenyl internal standard.
[d]Measured by Inductively Coupled Plasma.
[e]Was not measured.

TABLE 3

Effect of Reaction Concentration on Displacement Rates and Yields

| % Solids at Which Reaction Was Run | % C6B Catalyst | HPLC Yield | Isolated Yield |
|---|---|---|---|
| 15 | 2.5 | 74.9 | 74.2 |
| 20 | 2.5 | 82.6 | 82.1 |
| 30 | 2.5 | 87.3 | 89.9 |
| 40 | 2.5 | 96.5 | 96.0 |
| 50 | 2.5 | 98.0 | 98.3 |

EXAMPLE 9

Exchange Reaction with Butylbisimide and Synthesis of BPADA

Two exchange reactions synthesizing bisphenol-A dianhydride ("BPADA") from bisphenol-A bisbutylimide, phthalic anhydride, triethylamine and water were conducted. These examples illustrate that the alkylamines according to this invention can be run at a solids level reaction higher than that typical of prior art exchange reactions, e.g., less than 30% by weight solids. The higher solids reactions obtain higher throughput in the plant and lower phthalic anhydride ("PA") concentration in recycle.

a. Reaction Having 44% by Weight Solids

The apparatus used for this exchange reaction was a one liter autoclave manufactured by Parr Associates equipped with mechanical stirring, a vent port with external valve, a sampling port consisting of a tube which extends nearly to the bottom of the inside of the vessel and an external valve, an addition port with valve, a pressure gauge, a thermocouple well for measuring temperature and a safety pressure release valve. A stainless steel bottle with valves at both ends was attached to the addition port. One end of the bottle was connected to a high pressure nitrogen line for the purposes of pressurizing the bottle. Both the autoclave and the addition bottle had thermocouple wells for temperature measurement and were wrapped with heating tape which was plugged into a variable transformer for temperature control. Additionally, the autoclave was placed on a hot plate which also was used as a heat source.

Bisphenol-A bisbutylimide was prepared by imidizing 2 moles bisphenol-A dianhydride (BPADA) with 2 moles of fleshly distilled n-butylamine in acetic acid. The reaction was run for five hours. Acetic acid was removed via distillation, followed by a toluene wash to azeotropically remove the last traces of acetic acid. The toluene/bisimide solution then was stripped of toluene on a rotary evaporator, thereby providing a viscous oil. The oil was dissolved in 3:1 ratio of ethanol/ethyl acetate at reflux and then cooled to produce white crystals having a melting point in the range of 92°–94° C. The bisimide was then eluted through silica gel using toluene as an eluant to provide, upon solvent removal, a white powder.

The stainless steel addition bottle was charged with 63.0 grams (0.100 moles) of bisphenol-A bisbutylimide and purged with nitrogen. The autoclave was charged with 88.872 grams (0.6000 mole) phthalic anhydride, 91.071 grams (0.9000 moles) triethylamine (TEA), and 104.12 grams of water and then purged with nitrogen. The molar ratio of phthalic anhydride to bisimide thus was 6 and the ratio of triethylamine to phthalic anhydride was 1.5. The reaction mixture contained 30% by weight water.

The autoclave and addition bottle were both heated to 210° C. before pressurizing the bottle to a pressure greater than that in the autoclave. To the stirring autoclave mixture was then added the molten bisimide from the addition bottle by opening the valve on the bottle.

Samples were removed from the sample port after 30 and 60 minutes for workup and analysis. These samples were stripped of solvent by heating the samples for 5 minutes at 250° C. and 2–10 torr to remove volatiles and to ring close the tetraacid triethylamine salts to dianhydride and any residual amide acids to imides. The resulting materials were cooled to room temperature and analyzed to determine the percent exchange.

Equilibrium of the statistical reaction mixture was reached after 30 minutes. The percent exchange was about 73–77%.

b. Reaction Having 54% by Weight Solids

The same apparatus and procedure used in the low solids level exchange were used in the high solids level reaction. The addition bottle was charged with 63.0 grams (0.100 moles) of bisphenol-A bisbutylimide, prepared as described for the low solids level reactions, and then purged with nitrogen. The autoclave was charged with 59.25 grams (0.4000 mole) phthalic anhydride, 48.5767 grams (0.4800 moles) triethylamine (TEA), and 55.6 grams of water, thereby running the reaction with a phthalic anhydride/ bisimide ratio of 4.0 and a triethylamine/phthalic anhydride ratio of 1.2. The exchange reaction reached equilibrium in about 40 minutes, and resulted in about 58–62% exchange.

The advantage of the butyl system over the methyl system is that BuPl, butylimideanhydride and butylbisimide have a greater solubility in toluene than the methyl analogs. Therefore, the column extraction efficiency will be greater and result in increased hydraulic loading to the column (increased throughput, almost doubled, and lower operating costs). Energy savings in stripping toluene also result.

EXAMPLE 10

Zone Refining

The solventless purification of 4-NPBI was achieved through the implementation of zone-refining methodology. The purification procedure was performed by loading crude molten 4-NPBI (m.p.88°–92° C.; pure 4-NPBI m.p. 94°–95° C.) into a quartz (or pyrex) reactor tube, and allowing the dark yellow-orange liquid to solidify. The reactor tubes were 71 cm long with an outside diameter of 11–14 mm and an inside diameter of 6–11 mm. The tube reactors were mounted vertically in a double-pass zone-melting apparatus. The two furnaces were initially set at 89±1° C. The purification process was studied by heating in either the upward or the downward direction. The heater transverse rate was set between 2 and 8 inches per hour. The process was cycled through from 1 to 25 passes.

Under the reaction conditions, the major contaminants moved in the direction of increasing gravity (downward):

i.e. 3-nitro-N-butylphthalimide (3-NPBI; m.p. 68°–70° C.), N-butylphthalimide (N-BPI; m.p. 32°–35° C.). However, the data indicate that some of the more highly colored compounds enrich in the direction the furnaces move: i.e. 4-nitro-N-(3-nitrooxybutyl)phthalimide (Bob3; m.p. 67°–68° C.), and 4-nitro-N-(4-nitrooxybutyl)phthalimide (Bob4). In general, the concentrations of all the contaminants could be reduced such that the crude 4-NPBI was greater than 99+% pure. Furthermore, the purified materials exhibited substantially lower YI values than did the initial crude 4-NPBI.

Section A (Zone-Refining):

Crude 4-NPBI was melted (approximately 95° C.); the 4-NPBI was obtained from one of the following sources: CRD pilot plant (mixed acid source), Mt. Vernon Hot Nitric (no washes), or Mt. Vernon Hot Nitric (Bobs removed). The resulting yellow-orange liquid 4-NPBI was poured into a 1 mm thick-walled quartz tube (o.d. 12 mm; i.d. 10 mm; length 71 cm); six to eight inches of purified sand had been loaded into the reactor tube previously, to provide both a heat-up zone for the furnaces and sufficient room to attach the tube reactor to the zone-refiner. The sample was added into the tube reactor until roughly a 6 inch head space remained. The liquefied material was allowed to solidify. The reactor tube was then loaded into a table-top, vertical-mount, twin-pass-melting apparatus. The reactor tube was capped with a nitrogen bubbler to allow for any out-gassing within the reactor environment. The two furnaces were initial set at 89±1° C.

The samples were heated in only one vertical direction at a time. Heating in either direction was found to have its own advantage or disadvantage depending on the source of the 4-NPBI. The furnaces were turned off during the recycle stage where they moved from the end of the reactor tube back to the starting point; heat-up and cool-down delays were programmed into each run cycle such that the furnaces were close to thermal equilibrium before they began moving in either direction. Heating in both directions (ovens always on) was not examined. The furnaces traversed the reactor vessel at 4 inches per hour. A total of 3 to 10 passes were examined.

Upon completion of the purification procedure, the color of the crystalline 4-NPBI in the reactor was noted to range from white to light yellow depending on its position in the reactor. Starting at the 4-NPBI apex, the material was analyzed in 4–6 inch sections using standard HPLC procedures.

General Nomenclature/abbreviations Note: 4-nitro-N-(3-hydroxybutyl)phthalimide (3-OH), 4-nitro-N-(4-hydroxybutyl)phthalimide (4-OH), 4-nitrophthalimide (4-NPIH), and 4-nitro-N-(x-nitrooxybutyl)phthalimide (Bobx)

Run 1: Hot Nitric, No Bobs (MV 86-48; HN 4-NPBI pp.275)

The crude 4-NPBI (35 g; 0.134 mol) was melted and loaded into a quartz tube reactor as described above. The tube reactor was loaded into zone-refining apparatus once the material had resolidified. The ovens were initially set at 89±1° C. Heating was in the upward direction with an oven transversal rate of 4 inches per hour. After three cycles, the oven temperatures were raised to 95±1° C. Three more cycles were completed before the purification process was terminated; the progress of the purification procedure was via visual inspection. Sampling of the purified 4-NPBI was at approximately four inch intervals along the reactor tube starting at the top of the purified solid. The sample analyses were as follow:

Initial Crude Mixture: (yellow-orange crystalline mass) 4-NPBI (95.434%), 3-NPBI (4.496%), INT C═C (0.057%), 3-OH (0.011%), and 4-NPIH (0.003%)

Samples 1 & 2: (light yellow crystalline solid) 4-NPBI (98.448%), 3-NPBI (1.497%), INT C═C (0.047%), and 3-OH (0.008%).

Sample 5 (above sand): (white crystalline solid) 4-NPBI (99.922%) and 3-NPBI (0.078%).

Sample 6 (sand residue): (dark orange-yellow solid) 4-NPBI (71.829%), 3-NPBI (27.896%), N-BPI (0.148%), INT C═C (0.093%), 3-OH (0.0207%), 4-NPIH (0.014%), and 4-OH (0.007%).

A second attempt at purification of this material produced similar results. For example:

Sample 5 (above sand; 2nd Run): (white crystalline solid) 4-NPBI (99.716%), 3-NPBI (0.219%), INT C═C (0.053%), 3-OH (0.009%), and 2-OH (0.003%).

Run 2: Hot Nitric, No Washes (MV)

The impure 4-NPBI (40 g; 151 mol) was loaded, run, and analyzed as in Run 1. The initial 4-NPBI mixture was found to have the following composition: (orange solid mass) 4-NPBI (93.706%), 3-NPBI (3.991%), highly polar material (1.187%), 4-NPIH (0.180%), Bob3 (0.137%), 3-OH (0.110%), 2-OH (0.108%), and 4-OH (0.046%). After purification, the analyses of the segments indicated the following:

Sample 1 (top): (light yellow crystalline solid) 4-NPBI (98.598%), 3-NPBI (0.491%), Bob3 (0.259%), 3-OH (0.137%), 2-OH (0.060%), 4-NPBI (0.043%), and 4-OH (0.031%).

Sample 2: (light yellow crystalline solid) 4-NPBI (98.807%), 3-NPBI (0.155%), Bob3 (0.355%), 3-OH (0.179%), 2-OH (0.058%), 4-OH (0.020%), and 4-NPIH (0.018%).

Sample 5 (sand residue): (orange-yellow solid) 4-NPBI (78.850%), 3-NPBI (15.940), highly polar material (3.264%), 4-NPIH (0.511%), 3-OH (0.249%), 4-OH (0.084%), and 2-OH (0.045%).

Run 3: CRD Pilot Plant, Mixed Acid Source.

The crude 4-NPBI (16 g; 0.064 mol) was loaded and run as per Run 1. The initial mixture was determined to contain the following: 4-NPBI (97.351%), 3-NPBI (2.058%), 3-OH (0.167%), and N-BPI (0.108%). After purification the following compositions were found:

Sample 1: (White crystalline solid) 4-NPBI (99.287%), 3-NPBI (0.405%), 3-OH (0.119%), and N-BPI (0.005%).

Sample 2: (White crystalline solid) 4-NPBI (98.028%), 3-NPBI (1.543%), 3-OH (0.136%), and N-BPI (0.071%).

Sample 3: (Light yellow crystalline solid) 4-NPBI (97.221%), 3-NPBI (2.256%), 3-OH (0.113%), and N-BPI (0.120%).

Sample 4: (Light yellow crystalline solid) 4-NPBI (96.608%), 3-NPBI (2.224%), highly polar material (0.374%), 3-OH (0.507%), and N-BPI (0.127%).

Section B. (Displacement Chemistry):

General procedures for the displacement reaction: The toluene used for the displacement reactions was distilled from sodium/benzophenone ketyl immediately prior to use. The disodium salt of bisphenol-A (BPA) was supplied by General Electric as a toluene slurry. The removal of toluene was accomplished by heating the salt under vacuum ($1 \times 10^{-4}$ mm Hg). The drying temperature was raised incrementally, with a final drying stage of 160° for 8 hours; the dried salt was subsequently stored in a Vacuum Atmospheres Dri Lab glovebox for further use. The 4-NPBI was azeotropically dried using toluene, immediately prior to running the displacement reaction. The C6B (bis(tri-n-butylammonium)-1,6-hexane dibromide) was provided by the Five Starr Group, inc. and used without further purification. The HPLC conditions for the displacement reaction analyses utilize an ODS-18 reverse phase Whatman column and a linear solvent gradient program (solvent ratio$_{initial}$V/V $H_2O:CH_3CN$ of 56:44; solvent ratio$_{final}$ 100% $CH_3CN$). The total time for HPLC analysis program was 24 minutes. An internal standard (1, 3, 5-triphenylbenzene; 285 nm wavelength monitor) was used to calibrate each HPLC chromatogram. The following examples illustrate the general reaction procedures:

Run 1. Zone-Refined Sample 1 (4-9-90: Hot Nitric; No Washes)

A 50 ml round-bottomed two-necked flask equipped with a stir bar, reflux condenser, and a nitrogen bubbler was used for the reaction. The reaction flask was loaded with 2.8440 g (10.4 mmol) of zone-refined 4-NPBI, 1.422 g (5.0 mmol) of BPA disodium salt, 0.0379 g (0.06 mmol) of C6B, 0.1686 g of triphenylbenzene (standard), and 5 ml of toluene. The reaction vessel was placed in an oil bath preheated to 140° C. The overall reaction mixture contained 45% solids. Aliquots were taken at 5 min. intervals. Each aliquot was quenched into a solution (10 ml) derived from a mixture of acetonitrile (500 ml), methanol (50 ml), and a glacial acetic acid (5 ml). After 2 h, HPLC analysis indicated that the conversion to BPA-bisimide had only reached 16%. It was later determined through HPLC analysis that this particular zone-refined sample contained a nitrate ester (Bob3; 0.259%) detrimental to both the product rate and yield in the displacement reaction.

Run 2. Zone-Refined Sample 5 (nitrate ester removed (No Bobs): MV 86-48; HN 4-NPBI)

The reaction was repeated with a reactor vessel outfitted as in Run 1. The materials used were: 4-NPBI (1.6094 g; 6.4 mmol), BPA disodium salt (0.8834 g; 3.2 mmol), C6B (0.0236 g; 0.03 mmol), 1, 3, 5-triphenylbenzene (standard: 0.1498 g), and toluene (3 ml). The reaction mixture contained 45% solids. It was heated at 140° C. Aliquots were taken and analyzed as described previously. The displacement reaction was found to be complete within 15 minutes. The solution work-up involved cooling the reaction mixture down to 80° C. The cooled solution was stirred for 15 minutes in the presence of 5% NaOH$_{aq}$ (base wash); the organic to aqueous volume ratio was 4:1. The isolated yield of the desired product was 85%. This material produced a YI number of 6.4. The monoimide level was ca. 0.96%.

Run 3. Zone-Refined Sample 5 (2nd Purification run; Nitrate ester removed as in Run 2 starting material)

The reaction was repeated with a reactor vessel outfitted as in Run 1. The materials used follow: 4-NPBI (1.58 g), BPA disodium salt (0.86 g), C6B (0.023 g), 1, 3, 5-triphenylbenzene (standard: 0.146 g), and toluene (2.5 ml). The reaction mixture contained 45% solids. It was heated at 140° C. Aliquots were taken and analyzed as described previously. The displacement reaction was found to be complete within 20 minutes; the reaction was stirred for a total time of one hour. The solution work-up involved cooling the reaction mixture down to 80° C. The cooled solution was stirred for 15 minutes in the presence of 5% NaOH$_{aq}$ (base wash); the organic to aqueous volume ratio was 4:1. The monoimide level was ca. 0.96%.

The above clearly demonstrates that 4-nitro-N-butylphthalimide (4-NPBI) can be readily converted to an analytically pure grade of material, through the use of zone-melting (zone-refining) techniques. The purified 4-NPBI was subsequently shown to undergo facile conversion to the bisbutylimide of BPA dianhydride in high yield. The resulting bisbutyl bisimide exhibited color numbers (YI=6.4) comparable to those now obtained for the bismethyl bisimide process, under current plant operation.

From the above it has also been concluded that other solventless, melt methods of purification of the 4-NPBI (or its analogues) such as melt crystallization process can be employed commercially. In a melt crystallization process, there will be no oven movement; hence, all the impurities in the crude 4-NPBI will flow out the bottom of the reactor (no furnace tracking problems as with zone-refining).

TABLE 5

| ALKYL GROUP vs PHYSICAL PROPERTIES | | | | | | | | | | | |
|---|---|---|---|---|---|---|---|---|---|---|---|
| Alkyl Group | | Methyl | Ethyl | Propyl | Butyl | Hexyl | Dodecyl | i-Propyl | i-Butyl | t-Butyl | n-Octyl |
| Imide | MP[1] = | 133 | 78 | 66 | 35 | 37 | 65 | 84 | 95 | 61 | — |
|  | BP[2] = | 275 | 273 | 285 | 298 | 327 | — | 296 | 275 | 279 | — |
|  | Sol[3] = | 6.7% | 22 | 27 | >70% | 24% | 21 | 25 | 22 | 18 | — |
| Nitro | MP = | 176 | 107 | 102 | 92 | 95 | 89 | 133 | 128 | 127 | 88 |
| Imide | BP = | 334 | 330 | 325D | 290D | — | — | 320D | 329D | — | — |
|  | Sol = | 2.0% | 22 | 33 | >50% | 34% | 24 | 11 | 18 | 29 | — |
| BPA[4]- | MP = | 147 | 148 | 111 | 94 | 92 | OIL | 126 | — | — | — |
| Bisimide | Sol = | 20% @ 80° C. | 20 | 50 | 100 | 100 | 100 | 44 | — | — | — |
| BP[5]- | MP = | 198[7] | 211 | 207[7] | 170[7] | 135 | 137 | 170 | — | — | — |
| Bisimide | Sol = | <1% @ 80° C. | 7% | <1[7] | 20% | >90%[7] | 100 | <1 | — | — | — |
| Oxy[6]- Bisimide |  | 265 | — | — | 116 | — | — | — | — | — | 102 |

[1]MP = melting point in °C.
[2]BP = boiling point in °C.
[3]Sol = solubility in toluene at room temperature
[4]BPA = bisphenol A bisimide
[5]BP = biphenyl bisimide
[6]Oxy = bisimide of oxydianhydride
[7]These values are not the same as those for the materials illustrated in Table 1. The discrepancies could be due to the level of impurites in the different samples used to obtain these values reported here.
— = not determined
OIL = material was not a crystalline solid having a discrete melting point. The material is simply a viscous liquid.

What is claimed:

1. A process for preparing an N-alkyl nitrophthalimide suitable for preparing bisimides and bis(ether anhydrides), comprising:
    (a) reacting an N-($C_3$–$C_6$)alkyl phthalimide and a nitrating agent to form an N-($C_3$–$C_6$)alkyl nitrophthalimide;
    (b) removing substantially all of the nitrating agent; and
    (c) purifying the N-($C_3$–$C_6$)alkyl nitrophthalimide by liquid/liquid extraction of a molten N-($C_3$–$C_6$)alkyl nitrophthalimide phase using an aqueous medium, by vacuum distillation, or by zone refining.

2. The process of claim 1, wherein said nitration step (a) comprises nitrating said N-alkyl phthalimide in the presence of a nitrating media comprising concentrated sulfuric acid and nitric acid.

3. The process of claim 2, wherein the concentration of said sulfric acid ranges from about 70% to about 102%.

4. The process of claim 3, wherein the concentration of said sulfric acid ranges from about 95% to about 100%.

5. The process of claim 2, wherein the concentration of said nitric acid ranges from about 60% to about 99%.

6. The process of claim 5, wherein the concentration of said nitric acid ranges from about 90% to about 99%.

7. The process of claim 2, wherein the percent solids in said nitration step ranges from about 10% to about 50% by weight.

8. The process of claim 7, wherein the percent solids in said nitration step ranges from about 25% to about 35% by weight.

9. The process of claim 2, wherein the amount of the nitrating agent is sufficient to substantially minimize the side oxidation of N-alkyl phthalimide to 4-nitro-(3-hydroxy alkyl) phthalimide.

10. The process of claim 9, wherein the amount of said nitrating agent is less than 3% by weight of the reaction mixture.

11. A process according to claim 1 wherein the nitrating agent is nitric acid at a concentration by weight of at least about 94%.

12. A process according to claim 1 wherein the N-alkyl nitrophthalimide has a melting temperature in the range of about 90° to about 135° C.

13. A process according to claim 1, wherein the N-$(C_3-C_6)$alkyl phthalimide is n-propyl phthalimide, n-butyl phthalimide, or n-hexyl phthalimide.

14. A process according to claim 1 further comprising (d) drying the N-$(C_3-C_6)$alkyl nitrophthalimide under substantially solventless conditions.

15. A process according to claim 1 wherein when the N-$(C_3-C_6)$alkyl phthalimide is N-butyl phthalimide, and wherein the process further comprises, prior to step (c), a step of pretreating the resulting N-butyl nitrophthalimide with concentrated acid, and a subsequent dilute basic wash.

16. A process according to claim 15 wherein the concentrated acid is concentrated sulfuric acid.

17. A process according to claim 15 wherein the concentrated acid is about 95–98% by weight sulfuric acid and the dilute basic wash is about 0.2 to about 1% by weight base.

* * * * *